United States Patent [19]

Fuchs et al.

[11] 4,279,920

[45] Jul. 21, 1981

[54] 2,2-DIMETHYL-3-(2-BROMO-2-PHENYL-VINYL)-CYCLOPROPANECARBOXYLIC ACID 3-PHENOXYBENZYL ESTERS AND PESTICIDAL USE

[75] Inventors: Rainer Fuchs; Hellmut Hoffmann, both of Wuppertal; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 74,045

[22] Filed: Sep. 10, 1979

[30] Foreign Application Priority Data

Sep. 29, 1978 [DE] Fed. Rep. of Germany ....... 2842542

[51] Int. Cl.$^3$ .................... A01N 43/30; C07C 69/743; C07C 121/75
[52] U.S. Cl. .............................. 424/282; 260/465 D; 424/304; 424/308; 542/429; 560/8; 560/18; 560/65
[58] Field of Search ................. 260/465 D; 560/8, 18, 560/65; 424/304, 308, 282; 542/429

[56] References Cited

U.S. PATENT DOCUMENTS

| 3,973,036 | 8/1976 | Hirano et al. | 424/304 |
| 4,024,163 | 5/1977 | Elliott et al. | 260/347.4 |
| 4,157,447 | 6/1979 | Engel | 560/8 |
| 4,199,596 | 4/1980 | Fuchs et al. | 424/304 |

Primary Examiner—Dolph H. Torrence
Attorney, Agent, or Firm—Sprung, Felfe, Horn, Lynch & Kramer

[57] ABSTRACT 2,2-Dimethyl-3-(2-bromo-2-phenyl-vinyl)-cyclopropanecarboxylic acid 3-phenoxybenzyl ester of the formula

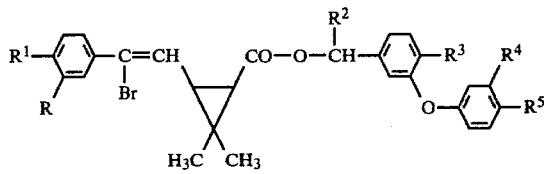

which possess arthropodicidal properties. In addition, the new intermediate of the formula

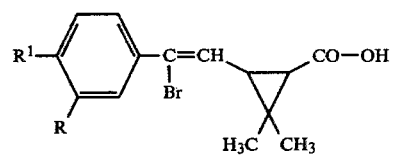

is produced by reacting an α-bromo-benzyl-phosphonic acid ester of the formula

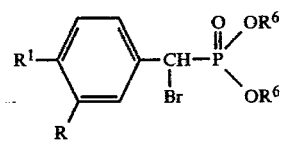

in which $R^6$ each independently is alkyl or phenyl, or the two radicals $R^6$ together are alkanediyl, with a 3-formyl-2,2-dimethyl-cyclopropanecarboxylic acid ester and saponifying. Also the compounds of the formula

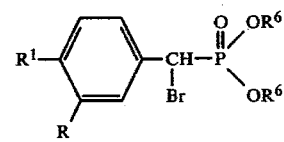

which are new when $R^1$ is not alkyl, are produced by reacting triphenylphosphine and bromine to form dibromo-triphenylphosphorane, and reacting the dibromo-triphenylphosphorane without isolation with an α-hydroxy-benzyl-phosphonic acid ester of the formula

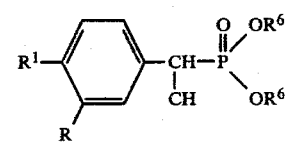

10 Claims, No Drawings

2,2-DIMETHYL-3-(2-BROMO-2-PHENYL-VINYL)-CYCLOPROPANECARBOXYLIC ACID 3-PHENOXYBENZYL ESTERS AND PESTICIDAL USE

The present invention relates to and has for its objects the provision of particular new 2,2-dimethyl-3-(2-bromo-2-phenyl-vinyl)-cyclopropanecarboxylic acid 3-phenoxybenzyl esters which possess arthropodicidal properties, active compositions in the form of mixtures of such compounds with solid and liquid dispersible carrier vehicles, and methods for producing such compounds and new intermediates therefor, and for using such compounds in a new way especially for combating pests, e.g. insects and acarids, with other and further objects becoming apparent from a study of the within specification and accompanying examples.

It is known that certain styryl-cyclopropanecarboxylic acid phenoxybenzyl esters, for example 3-(2-phenyl-vinyl)- and 3-(2-chloro-2-phenyl-vinyl)-2,2-dimethyl-cyclopropanecarboxylic acid 3-phenoxy-benzyl ester, are insecticidally and acaricidally active (see DE-OS (German Published Specification) No. 2,738,150). However, the action of these compounds is not always satisfactory, especially at low concentrations of active compound and when low amounts are used.

The present invention now provides:

(1), as new compounds, the substituted bromostyryl-cyclopropanecarboxylic acid phenoxybenzyl esters of the general formula

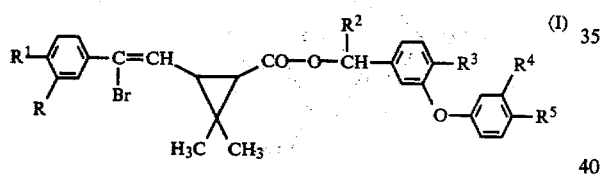

in which
R represents hydrogen, halogen, alkyl or alkoxy,
R¹ represents hydrogen, halogen, alkyl, alkoxy or alkylthio or
R and R¹ together represent methylenedioxy,
R² represents hydrogen, cyano or ethynyl and
R³, R⁴ and R⁵ are selected independently and each represent hydrogen or halogen, with the proviso that at least one of R³, R⁴ and R⁵ represents halogen;

(2) a process for the preparation of a bromostyryl-cyclopropanecarboxylic acid phenoxybenzyl ester of the formula (I), in which a bromostyryl-cyclopropanecarboxylic acid of the general formula

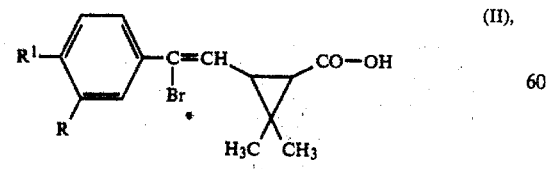

in which R and R¹ have the meanings stated under (1), or a reactive derivative thereof, is reacted with a substituted phenoxybenzyl alcohol of the general formula

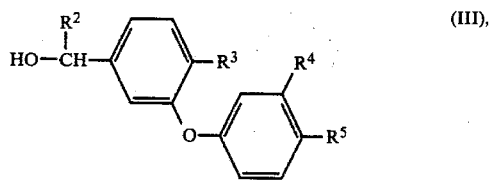

in which R², R³, R⁴ and R⁵ have the meanings stated above, or a reactive derivative thereof, if appropriate in the presence of an acid acceptor and if appropriate using one or more diluents:

(3), as new compounds, the bromostyrylcyclopropanecarboxylic acids of the general formula

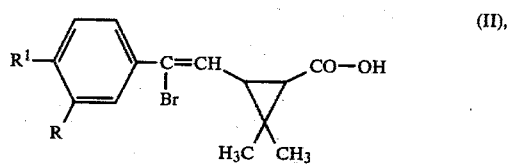

in which R and R¹ have the meanings stated under (1);

(4) a process for the preparation of a bromostyrylcyclopropanecarboxylic acid of the general formula (II), in which an α-bromo-benzyl-phosphonic acid ester of the general formula

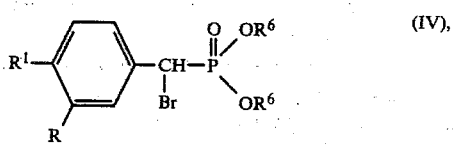

in which
R and R¹ have the meanings stated under (1) and each
R⁶ represents alkyl or phenyl, or the two radicals R⁶ together represent alkanediyl,
is reacted with a formyl-cyclopropanecarboxylic acid ester of the general formula

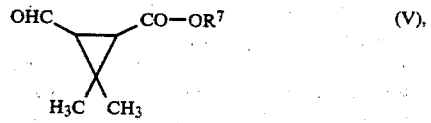

in which R⁷ represents alkyl, in the presence of a base and if appropriate using a diluent, and the bromostyryl-cyclopropanecarboxylic acid ester thereby formed is saponified by a known method, for example by heating with sodium hydroxide in aqueous alcohol, to give the corresponding bromostyryl-cyclopropanecarboxylic acid of the formula (II);

(5), as new compounds, the α-bromo-benzyl-phosphonic acid esters of the general formula

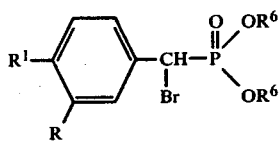
(IV a), in which
R has the meaning stated under (1),
$R^1$ represents hydrogen, halogen, alkoxy or alkylthio or, R and $R^1$ together represent methylenedioxy and
$R^6$ has the meaning stated under (4);

(6) a process for the preparation of an α-bromobenzyl-phosphonic acid ester of the formula (IV), in which an α-hydroxy-benzyl-phosphonic acid ester of the general formula

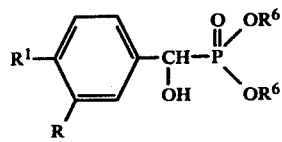
(VI), in which
R and $R^1$ have the meanings stated under (1) and $R^6$ has the meaning stated under (4), is reacted with dibromo-triphenylphosphorane (which is, if appropriate, formed in situ from triphenylphosphine and bromine) if appropriate in the presence of an acid acceptor and if appropriate using a diluent.

The new bromostyryl-cyclopropanecarboxylic acid phenoxybenzyl esters of the formula (I) are distinguished by a high insecticidal and acaricidal activity.

Surprisingly, the bromostyryl-cyclopropanecarboxylic acid phenoxybenzyl esters according to the invention exhibit a considerably higher insecticidal and acaricidal action than the compounds of analogous structure and the same type of action which are known from the state of the art.

Preferred bromostyryl-cyclopropanecarboxylic acid esters of the formula (I) are those in which R represents hydrogen, fluorine, chlorine, bromine, methyl or methoxy, $R^1$ represents hydrogen, fluorine, chlorine, bromine, methyl, methoxy or methylthio or R and $R^1$ together represent methylenedioxy, $R^2$ represents hydrogen, cyano or ethynyl and $R^3$, $R^4$ and $R^5$ are selected independently and each represent hydrogen or fluorine, with the proviso that at least one of $R^3$, $R^4$ and $R^5$ represents fluorine.

The general formula (I) also includes the various possible stereoisomers and optically active isomers and mixtures thereof.

In a preferred embodiment (a) of the process for the preparation of the compounds of the formula (I), as a reactive derivative of a bromostyryl-cyclopropanecarboxylic acid of the formula (II), the corresponding carboxylic acid chloride of the general formula

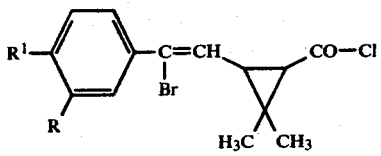
(VII), in which R and $R^1$ have the meanings stated above, is reacted with a substituted phenoxybenzyl alcohol of the general formula

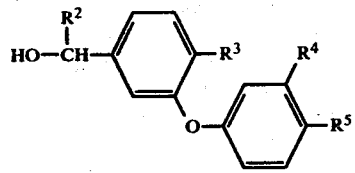
(III), in which $R^2$, $R^3$, $R^4$ and $R^5$ have the meanings stated above, if appropriate in the presence of an acid acceptor and if appropriate using a diluent.

A particularly preferred embodiment (b) of the process for the preparation of a compound of the formula (I) wherein $R^2$ represents cyano is characterized in that a carboxylic acid chloride of the general formula (VII) above is reacted with a substituted phenoxybenzaldehyde of the general formula

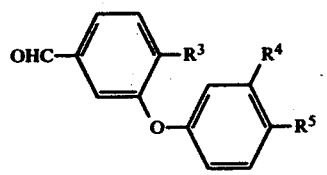
(VIII), in which $R^3$, $R^4$ and $R^5$ have the meanings stated above, in the presence of at least an equimolar amount of an alkali metal cyanide (preferably sodium cyanide or potassium cyanide), if appropriate in the presence of a catalyst and if appropriate using a diluent.

If, for example, 3-(2-bromo-2-(4-methoxy-phenyl)-vinyl)-2,2-dimethyl-cyclopropanecarboxylic acid chloride and 3-(3-fluoro-phenoxy)-benzyl alcohol are used as starting substances in process embodiment (a) and 3-(2-bromo-2-(3,4-dichloro-phenyl)-vinyl)-2,2-dimethyl-cyclo-propanecarboxylic acid chloride, sodium cyanide and 3-(4-fluorophenoxy)-4-fluoro-benzaldehyde are used as starting substances in embodiment (b), the corresponding reactions can be outlined by the following equations:

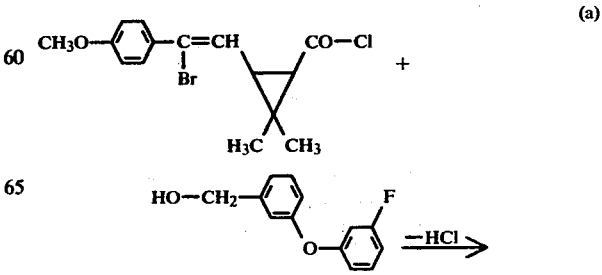
(a)

-continued

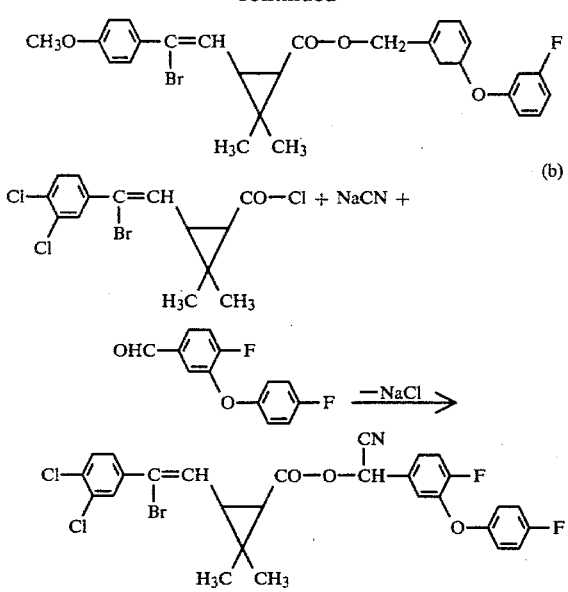

The formulae (II), (III), (VII) and (VIII) provide definitions of the starting substances to be used. Preferably, in these formulae, R to $R^5$ have the meanings that have been mentioned as preferred in the case of the definition of R to $R^5$ in formula (I).

The bromostyryl-cyclopropanecarboxylic acids (II) and the corresponding acid chlorides (VII), as reactive derivatives thereof, to be used as starting compounds are new.

The carboxylic acids of the formula (II) are obtained from the corresponding alkyl esters, preferably the methyl esters or ethyl esters, by saponification, that is to say by heating to temperatures between 50° and 150° C. for several hours, for example with sodium hydroxide in aqueous alcohol. Working up is effected in the customary manner, for example by stripping off the alcohol in vacuo, diluting the residue with water, acidifying the aqueous phase, extracting the organic phase with methylene chloride and drying it and stripping off the solvent.

The esters corresponding to the carboxylic acids of the formula (II) are obtained, as outlined under (4) above, by reacting α-bromo-benzyl-phosphonic acid esters of the formula (IV) above with formyl-cyclopropanecarboxylic acid esters of the formula (V) above in the presence of a base, for example sodium methylate, and if appropriate using a diluent, for example ethanol or tetrahydrofuran, at a temperature between −10° and +50° C. Working up can be carried out in the customary manner, for example by diluting the reaction mixture with water and extracting it with methylene chloride, drying the organic phase, stripping off the solvent and distilling in vacuo the product which remains. The acid chlorides of the formula (VII) corresponding to the carboxylic acids of the formula (II) can be prepared by reacting the carboxylic acids (II) with a halogenating agent, for example thionyl chloride, if appropriate using a diluent, for example carbon tetrachloride, at a temperature between 10° and 100° C., and can be purified by vacuum distillation.

Examples which may be mentioned of the carboxylic acids of the formula (II) and of the corresponding acid chlorides (VII) and esters are: 3-(2-bromo-2-phenyl-vinyl)-, 3-(2-bromo-2-(4-fluoro-phenyl)-vinyl)-, 3-(2-bromo-2-(4-chloro-phenyl)-vinyl)-, 3-(2-bromo-2-(3-bromo-phenyl)-vinyl)-, 3-(2-bromo-2-(4-bromo-phenyl)-vinyl)-, 3-(2-bromo-2-(3-methyl-phenyl)-vinyl)-, 3-(2-bromo-2-(4-methyl-phenyl)-vinyl)-, 3-(2-bromo-2-(3-methoxy-phenyl)-vinyl)-, 3-(2-bromo-2-(4-methylthio-phenyl)-vinyl)-, 3-(2-bromo-2-(3,4-dichlorophenyl)-vinyl)-, 3-(2-bromo-2-(3,4-dimethylphenyl)-vinyl)-, 3-(2-bromo-2-(3,4-dimethoxy-phenyl)-vinyl)- and 3-(2-bromo-2-(3,4-methylenedioxy-phenyl)-vinyl)-2,2-dimethyl-cyclopropanecarboxylic acid and the corresponding acid chlorides, the methyl esters and the ethyl esters.

Formula (IV) provides a definition of the α-bromo-benzyl-phosphonic acid esters to be used as intermediate products. Preferably, in this formula, R and $R^1$ have those meanings which are mentioned as preferred in the case of the definition of R and $R^1$ in formula (I) and $R^6$ represents methyl, ethyl or phenyl, or the two radicals $R^6$ together represent 2,2-dimethyl-1,3-propanediyl.

Examples of the compounds (IV) are: α-bromo-benzyl-, α-bromo-4-fluoro-benzyl-, α-bromo-4-chloro-benzyl-, α-bromo-3-bromo-benzyl-, α-bromo-4-bromo-benzyl-, α-bromo-3-methoxy-benzyl-, α-bromo-4-methoxy-benzyl-, α-bromo-4-methylthio-benzyl-, α-bromo-3,4-dichloro-benzyl, α-bromo-3,4-dimethoxy-benzyl- and α-bromo-3,4-methylenedioxy-benzyl-phosphonic acid dimethyl ester, -phosphonic acid diethyl ester and -phosphonic acid diphenyl ester.

Some of the compounds of the formula (IV) are known (those wherein $R^1$=alkyl; see Zh. Obsc.Khim. 39 (1969), 1,253–1,256).

The α-bromo-benzyl-phosphonic acid esters of the formula (IV) are obtained, as outlined above under (6), by reacting α-hydroxy-benzyl-phosphonic acid esters of the formula (VI) above with dibromo-triphenylphosphorane, which is appropriately produced in situ from triphenylphosphine and bromine, if appropriate in the presence of an acid acceptor, for example pyridine, if appropriate using a diluent, for example methylene chloride, at a temperature between −50° and +50° C. (see Houben-Weyl, Methoden der organischen Chemie (Methods of Organic Chemistry), 4th edition (1960), Volume 5/4, pages 404–405, Thieme Verlag, Stuttgart).

Working up can be carried out by customary methods, for example by distilling off the diluent in vacuo, digesting the residue with ether, filtering off undissolved triphenylphosphine oxide and distilling off the ether in vacuo. The crude product which remains can be purified by vacuum distillation.

Formula (VI) above provides a definition of the α-hydroxy-benzyl-phosphonic acid esters which are used as intermediate products. Preferably, in this formula, R, $R^1$ and $R^6$ have those meanings which have already been mentioned as preferred in the case of the definition of R, $R^1$ and $R^6$ in formula (IV).

Examples of the compounds (VI) are: α-hydroxy-benzyl-, α-hydroxy-4-fluoro-benzyl-, α-hydroxy-4-chloro-benzyl-, α-hydroxy-4-bromo-benzyl-, α-hydroxy-3-bromo-benzyl, α-hydroxy-3-methoxy-benzyl-, α-hydroxy-4-methoxy-benzyl-, α-hydroxy-4-methylthio-benzyl-, α-hydroxy-3,4-dichlorobenzyl-, α-hydroxy-3,4-dimethoxy-benzyl- and α-hydroxy-3,4-methylenedioxy-benzyl-phosphonic acid dimethyl ester, -phosphonic acid diethyl ester and -phosphonic acid diphenyl ester.

Hydroxy-benzyl-phosphonic acid esters of the formula (VI) are known. In general, they are obtained by reacting aldehydes of the general formula

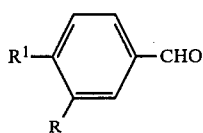

(IX), in which R and $R^1$ have the meanings stated above, with phosphorous acid esters of the general formula

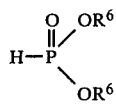

(X), in which $R^6$ has the meaning stated above, if appropriate in the presence of a catalyst, for example triethylamine, at a temperature of between 10° and 100° C. (see Houben-Weyl, Methoden der organischen Chemie (Methods of Organic Chemistry), 4th edition (1963), Volume 12/1, pages 475–483, Thieme Verlag, Stuttgart).

Examples of the aldehydes of the formula (IX), which are known compounds, are: benzaldehyde, 4-fluoro-benzaldehyde, 4-chloro-benzaldehyde, 4-bromo-benzaldehyde, 3-bromo-benzaldehyde, 3-methoxy-benzaldehyde, 4-methoxy-benzaldehyde, 3,4-dichloro-benzaldehyde, 3,4-dimethoxy-benzaldehyde and 3,4-methylenedioxy-benzaldehyde.

Examples of the phosphorous acid esters of the formula (X), which likewise are known compounds, are: phosphorous acid dimethyl ester (dimethyl phosphite), phosphorous acid diethyl ester (diethyl phosphite) and phosphorous acid diphenyl ester (diphenyl phosphite).

Formula (V) provides a definition of the formylcyclopropanecarboxylic acid esters also to be used as intermediate products. Preferably, in this formula, $R^7$ represents straight-chain or branched alkyl with 1 to 4 carbon atoms.

Examples of the compounds (V) are: 2,2-dimethyl-3-formyl-cyclopropanecarboxylic acid methyl ester, ethyl ester, n-propyl ester, iso-propyl ester, n-butyl ester, isobutyl ester, sec.-butyl ester and tert.-butyl ester.

The formyl-cyclopropanecarboxylic acid esters of the formula (V) are known, or they can be prepared by known processes, in general by reacting known alken-1-yl-cyclopropanecarboxylic acid esters with ozone (see U.S. Pat. No. 3,679,667).

Phenoxybenzyl alcohols of the formula (III) to be used as starting compounds for the preparation of the new bromostyryl-cyclopropanecarboxylic acid phenoxybenzyl esters (I), and the corresponding phenoxybenzaldehydes of the formula (VIII) are known, and they can be prepared analogously to known processes (see DE-OS (German Published Specification) Nos. 2,615,435 and 2,709,264).

Examples of the compounds (III) and (VIII) are: 3-(3-fluoro-phenoxy)-, 3-(4-fluoro-phenoxy)-, 3-phenoxy-4-fluoro-, 3-(3-fluoro-phenoxy)-4-fluoro- and 3-(4-fluorophenoxy)-4-fluoro-benzyl alcohol, 3-(3-fluoro-phenoxy)-, 3-(4-fluoro-phenoxy)-, 3-phenoxy-4-fluoro, 3-(3-fluorophenoxy)-4-fluoro- and 3-(4-fluorophenoxy)-4-fluoro-α-cyano-benzyl alcohol, 3-(3-fluorophenoxy)-, 3-(4-fluorophenoxy)-, 3-phenoxy-4-fluoro, 3-(3-fluoro-phenoxy)-4-fluoro- and 3-(4-fluoro-phenoxy)-4-fluoro-α-ethynyl-benzyl alcohol and 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-benzaldehyde.

All embodiments of the process for the preparation of the bromostyryl-cyclopropanecarboxylic acid phenoxybenzyl esters according to the invention are preferably carried out using a suitable solvent or diluent. Possible solvents or diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane ketones, such as acetone, methyl ethyl ketone, methyl isopropyl ketone and methyl isobutyl ketone; and nitriles, such as acetonitrile and propionitrile.

If the reaction is carried out in a two-phase medium, water is used as the second solvent component.

In the process of embodiment (a) described above, using an acid chloride of the formula (VII) and a phenoxybenzyl alcohol of the formula (III) as starting substances, any of the customary acid-binding agents can be used as the acid acceptor. Alkali metal carbonates and alcoholates, such as sodium carbonate and potassium carbonate, sodium methylate or ethylate and potassium methylate or ethylate and furthermore aliphatic, aromatic or heterocyclic amines, for example triethylamine, trimethylamine, dimethylaniline, dimethylbenzylamine and pyridine, have proved particularly suitable.

In the process embodiment (b) described above, using an acid chloride of the formula (VII) and a phenoxybenzaldehyde of the formula (VIII) as starting substances, a compound which usually serves as an auxiliary for the phase transfer of reactants in reactions in multi-phase media is in general used as a catalyst. Tetraalkyl- and trialkylaralkyl-ammonium salts, for example tetrabutylammonium bromide and trimethyl-benzyl-ammonium chloride, may be mentioned in particular.

The reaction temperature in all embodiments can be varied within a substantial range. In general, the reaction is carried out at from 0° to 100° C., preferably at from 10° to 50° C.

In general, the process according to the invention is carried out under normal pressure.

The starting substances are usually employed in equimolar amounts for carrying out the process according to the invention. An excess of one or other of the reactants brings no substantial advantages. In general, the reaction is carried out in one or more diluents in the presence of an acid acceptor or of a catalyst, and the reaction mixture is stirred at the required temperature for several hours. The reaction mixture is then shaken with toluene/water and the organic phase is separated off, washed with water and dried.

After distilling off the solvent in vacuo, the new compounds are in general obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. The refractive index is used for their characterization.

As already mentioned, the new bromostyryl-cyclopropanecarboxylic acid phenoxybenzyl esters are distinguished by a high insecticidal and acaricidal activity. They can be used against ectoparasites in the field of veterinary medicine.

The active compounds are well tolerated by plants, have a favorable level of toxicity to warm-blooded animals, and can be used for combating arthropod pests, especially insects and acarids (mites), which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Procellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderea, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis, bilobatus, Nephotettix cincticeps, Lecanium corni, Saissetia oleae, Laodelphax striatellus, Nilaparvata lugens, Aonidiella aurantii, Aspidiotus hederea,* Pseudococcus spp. and Psylla spp.;

from the order of the Lepidoptera, for example *Pectinophora gossypiella, Bupalus piniarus, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygam exigua, Mamestra brassicae, Panolis flammea, Prodenia litura,* Spodoptera spp., *Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aenus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., Monomorium pharaonis and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-in, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

The preparation of the novel compounds is shown in the following illustrative examples:

EXAMPLE 1:

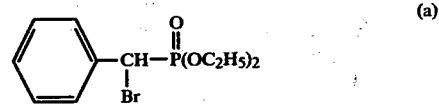

(a)

90 g of bromine, dissolved in 250 ml of methylene chloride, were added dropwise to a solution of 131 g (0.5 mol) of triphenylphosphine in 500 ml of methylene chloride at 30°–35° C., with exclusion of moisture. The mixture was subsequently stirred at room temperature for 1 hour, a solution of 122 g (0.5 mol) of α-hydroxybenzylphosphonic acid diethyl ester in 250 ml of methylene chloride was then added dropwise at −20° C. in the course of 1 hour, the mixture was subsequently stirred at −20° C. for 1 hour and 40 g of pyridine, dissolved in 250 ml of methylene chloride, were then added dropwise at −20° C. in the course of one hour. The mixture was subsequently stirred for 20 hours, the temperature slowly rising to +20° C. The reaction mixture was transferred to a pear-shaped flask and the solvent was distilled off under a waterpump vacuum. The residue was extracted by stirring with one liter of ether and the undissolved triphenylphosphine oxide was filtered off (120 g of triphenylphosphine oxide=86% of theory). The mother liquor was concentrated in vacuo and the residue was distilled under a high vacuum. 112 g (72% of theory) of α-bromobenzylphosphonic acid diethyl ester were obtained as a pale yellow oil with a boiling point of 110° C./0.01 mm Hg and a purity of 95.9% (gas chromatography).

The following compounds were obtained analogously:

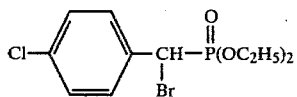

(Yield: 89.5% of theory; boiling point: 125° C./0.01 mm Hg),

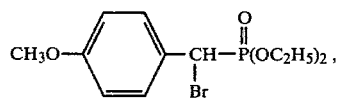

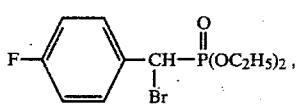

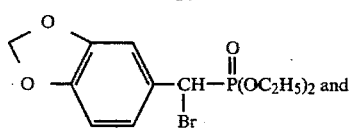 and

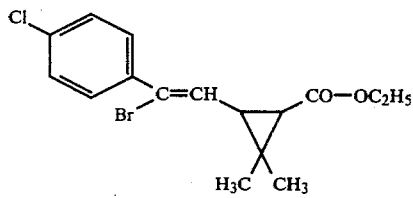

4.6 g (0.2 mol) of sodium were dissolved in portions in 100 ml of ethanol. When all the sodium had dissolved, 100 ml of tetrahydrofuran (anhydrous) were added, and 68.3 g (0.2 mol) of 4-chloro-α-bromo-benzyl-phosphonic acid diethyl ester, dissolved in 50 ml of anhydrous tetrahydrofuran, were added dropwise at 0° C., whilst stirring. After the mixture had been subsequently stirred at 0°–5° C. for a further 2 hours, 34 g (0.2 mol) of cis/trans-2,2-dimethyl-3-formyl-cyclopropanecarboxylic acid ethyl ester, dissolved in 50 ml of anhydrous tetrahydrofuran, were added dropwise at 0° C., whilst stirring. The mixture was then subsequently stirred at 20°–25° C. for a further 12 hours. 600 ml of water were then added to the reaction mixture and the mixture was extracted twice with 300 ml of methylene chloride each time. The organic phase was separated off and dried over magnesium sulphate, the solvent was distilled off under a waterpump vacuum and the residue was distilled in vacuo. 34.5 g (48.3% of theory) of 2,2-dimethyl-3-(2-bromo-2-(4-chloro-phenyl)-vinyl)-cyclopropanecarboxylic acid ethyl ester (cis, trans and E, Z isomer mixture) were obtained as a yellow oil with a boiling point of 160°–165° C./1 mm Hg.

The compound of the formula

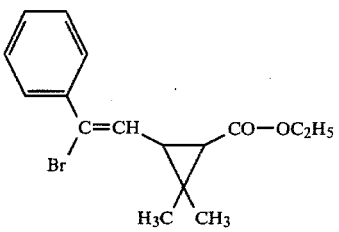

was obtained analogously in a yield of 50.2% of theory and with a boiling point of 140°–150° C./1 mm Hg.

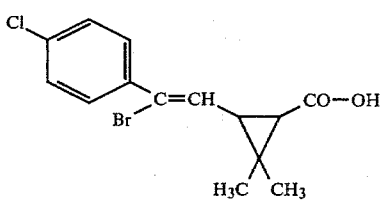

(c)

50 g (0.14 mol) of 2,2-dimethyl-3-(2-bromo-2-(4-chloro-phenyl)-vinyl)-cyclopropanecarboxylic acid ethyl ester were dissolved in 100 ml of ethanol, a solution of 6 g (0.15 mol) of sodium hydroxide in 100 ml of water was then added and the mixture was heated to the reflux temperature for 4 hours, while stirring. The ethanol was then distilled off under a waterpump vacuum, the residue was taken up in 300 ml of warm water and the mixture was extracted once with 300 ml of methylene chloride. The aqueous phase was separated off, acidified with concentrated hydrochloric acid and then extracted with 2 portions of 300 ml of methylene chloride. The organic phase was then separated off and dried over magnesium sulphate and the solvent was distilled off under a waterpump vacuum. Last residues of solvent were removed by brief incipient distillation under 2 mm Hg at a bath temperature of 60° C. 37.8 g (81.9% of theory) of 2,2-dimethyl-3-(2-bromo-2-(4-chlorophenyl)-vinyl)-cyclopropanecarboxylic acid (cis and trans, E and Z isomer mixture) were then obtained as a very viscous yellow oil. The structure was confirmed by the $^1$H-NMR spectrum.

$^1$H-NMR (in CDCl$_3$/TMS): aromatic H: 2.43–2.86τ(m, 4H), vinyl H: 3.33-3.57τ and 3.9-4.16τ(2m, 1H), cyclopropane H: 7.33-8.45τ(m/2H) and dimethyl H: 8.45-8.88(m/6H).

The compound of the formula

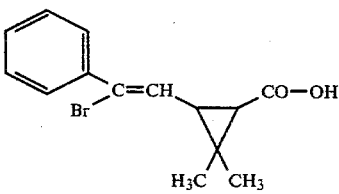

was obtained analogously in a yield of 78.6% of theory.

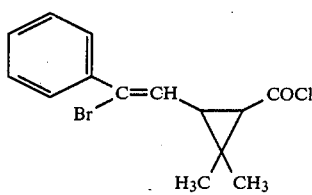
(d)

59 g (0.2 mol) of 2,2-dimethyl-3-(2-bromo-2-(4-chloro-phenyl)-vinyl)-cyclopropanecarboxylic acid were dissolved in 500 ml of carbon tetrachloride, and 119 g of thionyl chloride were slowly added dropwise at 25° C., while stirring. The mixture was then heated to the reflux temperature for 4 hours. When the reaction period had ended, excess thionyl chloride and carbon tetrachloride were distilled off under a waterpump vacuum. The oil which remained was distilled. 33.7 g (53.8% of theory) of 2,2-dimethyl-3-(2-bromo-2-(4-chloro-phenyl)-vinyl)-cyclopropanecarboxylic acid chloride were obtained as a colorless liquid with a boiling point of 165°–166° C. under 8 mm Hg.

The compound of the formula

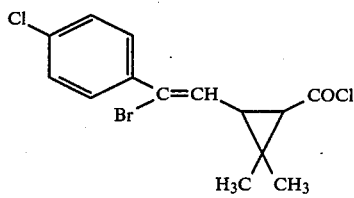

was obtained analogously in a yield of 92.5% of theory.

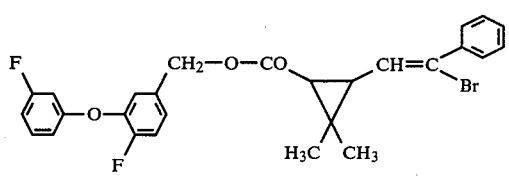
(e)

4.7 g (0.02 mol) of 3-(3-fluoro-phenoxy)-4-fluorobenzyl alcohol and 6.3 g (0.02 mol) of 2,2-dimethyl-3-(2-bromo-2-phenyl)-vinyl)-cyclopropanecarboxylic acid chloride were dissolved in 100 ml of anhydrous toluene, and 2.5 g of pyridine, dissolved in 50 ml of anhydrous toluene, were added dropwise at 20°–25° C., while stirring. Stirring was then continued at 25°–35° C. for 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 7.5 g (75.5% of theory) of 2,2-dimethyl-3-(2-bromo-2-phenyl-vinyl)-cyclopropanecarboxylic acid 4-fluoro-3-(3-fluorophenoxy)-benzyl ester were obtained as a yellow oil with the refractive index $n_D^{23}$: 1.5758.

EXAMPLE 2

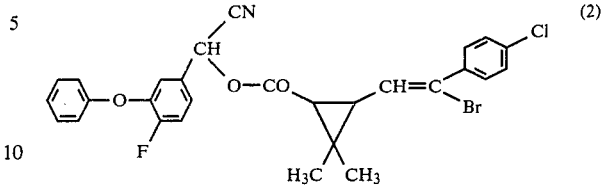
(2)

4.32 g (0.02 mol) of 3-phenoxy-4-fluoro-benzaldehyde and 6.96 g (0.02 mol) of 2,2-dimethyl-3-(2-bromo-2-(4-chlorophenyl)-vinyl)-cyclopropanecarboxylic acid chloride were together added dropwise to a mixture of 1.6 g of sodium cyanide, 2.5 ml of water, 100 ml of n-hexane and 0.5 g of tetrabutylammonium bromide at 20°–25° C., while stirring, and the mixture was then stirred at 20°–25° C. for 4 hours. 300 ml of toluene were then added to the reaction mixture and the mixture was extracted by shaking twice with 300 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 7.8 g (70.3% of theory) of 2,2-dimethyl-3-(2-bromo-2-(4-chloro-phenyl)-vinyl)-cyclopropanecarboxylic acid 3-phenoxy-4-fluoro-α-cyano-benzyl ester were obtained as a viscous oil. The structure was confirmed by the $^1$H-NMR spectrum.

$^1$H-NMR spectrum (CDCl$_3$/TMS): aromatic H: 7.65-6.8 δ (m/12H), benzyl H: 6.5-6.3 δ (m/1H), vinyl H: 6.6-6.4 δ and 6.1-5.9 δ (m/1H), cyclopropane H: 2.7-1.5 δ (m/2H), dimethyl H: 1.5-1.1 δ (m/6H).

The following compounds could be prepared analogously to Example 1 and/or 2:

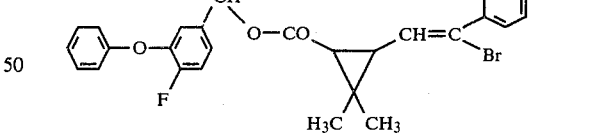
(3)

Yield: 73.1% of theory; refractive index $n_D^{23}$: 1.5799.

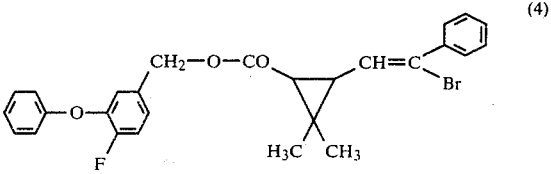
(4)

Yield: 85.5% of theory; refractive index $n_D^{23}$: 1.5882.

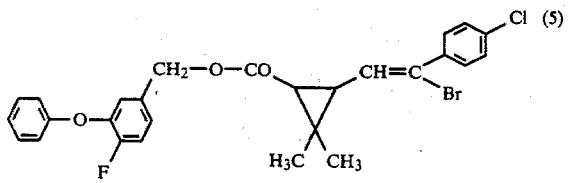

Yield: 74.6% of theory; refractive index $n_D^{23}$: 1.5943.

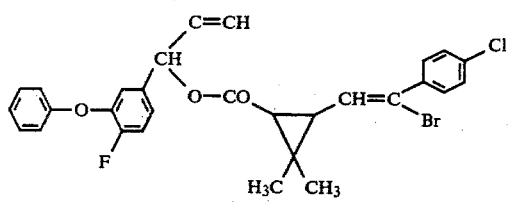

The insecticidal or acaricidal activity of the compounds of this invention is illustrated by the following examples wherein the compounds according to the present invention are each identified by the number (given in brackets) from preparative Examples 1 and 2 hereinabove.

EXAMPLE 3

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compounds showed a superior activity compared with the prior art: (3) (4), (5), (2) and (1).

EXAMPLE 4

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared with the prior art: (3) (4), (5), (2) and (1).

EXAMPLE 5

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (4), (5), (3), (2) and (1).

EXAMPLE 6

Test with parasitic fly larvae

Emulsifier: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared with the prior art: (4), (5), (3) and (1).

EXAMPLE 7

Test with parasitic adult cattle ticks (*Boophilus microplus* res.)

Solvent: alkylaryl polyglycol ether

To produce a suitable preparation of active compound, the active substance in question was mixed with the stated solvent in the weight ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compounds showed a superior action compared with the prior art: (4), (5), (3) and (1).

It will be appreciated that the instant specification and examples are set forth by way of illustration and not limitation, and that various modifications and changes may be made without departing from the spirit and scope of the present invention.

What is claimed is:

1. A 2,2-dimethyl-3-(2-bromo-2-phenyl-viyl)-cyclopropanecarboxylic acid 3-phenoxybenzyl ester of the formula

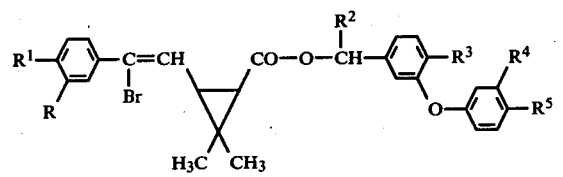

in which

R is hydrogen, halogen, alkyl or alkoxy, $R^1$ is hydrogen, halogen, alkyl, alkoxy or alkylthio, or R and $R^1$ together are methylenedioxy, $R^2$ is hydrogen, cyano or ethynyl, and $R^3$, $R^4$ and $R^5$ each independently is hydrogen or fluorine, with the proviso that at least one of $R^3$, $R^4$ and $R^5$ is fluorine.

2. A compound according to claim 1, in which

R is hydrogen, fluorine, chlorine, bromine, methyl or methoxy, $R^1$ is hydrogen, fluorine, chlorine, bromine, methyl, methoxy or methylthio, or R and $R^1$ together are methylenedioxy.

3. A compound according to claim 1, in which said compound is 2,2-dimethyl-3-(2-bromo-2-phenyl-vinyl)-cyclopropanecarboxylic acid 4-fluoro-3-(3-fluoro-phenoxy)-benzyl ester of the formula

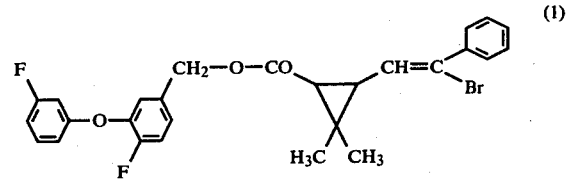

4. A compound according to claim 1, in which said compound is 2,2-dimethyl-3-(2-bromo-2-(4-chlorophenyl)-vinyl)-cyclopropanecarboxylic acid 3-phenoxy-4-fluoro-α-cyanobenzyl ester of the formula

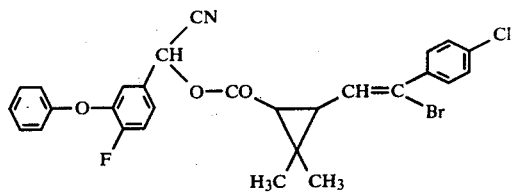

5. A compound according to claim 1, in which said compound is 2,2-dimethyl-3-(2-bromo-2-phenyl-vinyl)-cyclopropanecarboxylic acid 3-phenoxy-4-fluoro-α-cyano-benzyl ester of the formula

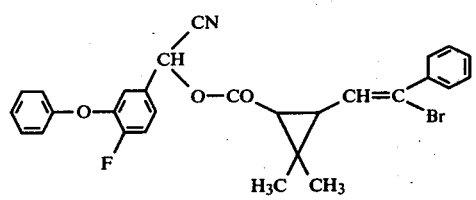

6. A compound according to claim 1, in which said compound is 2,2-dimethyl-3-(2-bromo-2-phenyl-vinyl)-cyclopropanecarboxylic acid 3-phenoxy-4-fluoro-benzyl ester of the formula

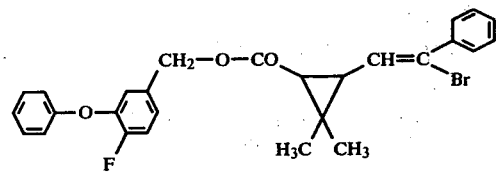

7. A compound according to claim 1, in which said compound is 2,2-dimethyl-3-(2-bromo-2-(4-chlorophenyl)vinyl)-cyclopropanecarboxylic acid 3-phenoxy-4-fluoro-benzyl ester of the formula

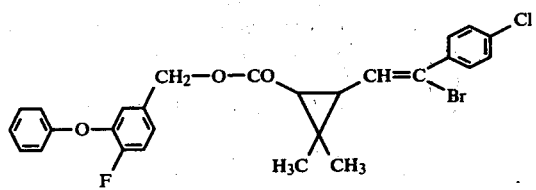

8. An arthropodicidal composition containing as active ingredient an arthropodically effective amount of a compound according to claim 1 in admixture with a diluent.

9. A method of combating arthropods which comprises applying to the arthropods, or to a habitat thereof, an arthropodically effective amount of a compound according to claim 1.

10. The method according to claim 9 wherein such compound is 2,2-dimethyl-3-(2-bromo-2-phenyl-vinyl)-cyclopropanecarboxylic acid 4-fluoro-3-(3-fluorophenoxy)-benzyl ester, 2,2-dimethyl-3-(2-bromo-2-(4-chlorophenyl)-vinyl)-cyclopropanecarboxylic acid 3-phenoxy-4-fluoro-α-cyano-benzyl ester, 2,2-dimethyl-3-(2-bromo-2-phenyl-vinyl)-cyclopropanecarboxylic acid 3-phenoxy-4-fluoro-α-cyano-benzyl ester, 2,2-dimethyl-3-(2-bromo-2-phenyl-vinyl)-cyclopropanecarboxylic acid 3-phenoxy-4-fluorobenzyl ester, or 2,2-dimethyl-3-(2-bromo-2-(4-chlorophenyl)-vinyl)-cyclopropanecarboxylic acid 3-phenoxy-4-fluorobenzyl ester, and it is applied to a domesticated animal.

* * * * *